United States Patent
Ikeda (10) Patent No.: US 9,627,858 B2
(45) Date of Patent: Apr. 18, 2017

(54) OBSERVATION PLUG AND SPARK OBSERVATION SYSTEM

(75) Inventor: Yuji Ikeda, Kobe (JP)

(73) Assignee: IMAGINEERING, INC., Hyogo (JP)

( * ) Notice: Subject to any disclaimer, the term of this patent is extended or adjusted under 35 U.S.C. 154(b) by 880 days.

(21) Appl. No.: 13/499,049

(22) PCT Filed: Sep. 30, 2010

(86) PCT No.: PCT/JP2010/067187
§ 371 (c)(1),
(2), (4) Date: Jun. 12, 2012

(87) PCT Pub. No.: WO2011/040589
PCT Pub. Date: Apr. 7, 2011

(65) Prior Publication Data
US 2012/0242982 A1   Sep. 27, 2012

(30) Foreign Application Priority Data

Sep. 30, 2009   (JP) .................. 2009-229088

(51) Int. Cl.
*G01N 21/00* (2006.01)
*H01T 13/48* (2006.01)
(Continued)

(52) U.S. Cl.
CPC ............... *H01T 13/48* (2013.01); *G01J 3/02* (2013.01); *G01J 3/0218* (2013.01); *G01J 3/36* (2013.01);
(Continued)

(58) Field of Classification Search
CPC .... G01J 1/10; G01J 5/00; H01T 13/40; G01L 3/26
(Continued)

(56) References Cited

U.S. PATENT DOCUMENTS 6,487,899 B1 * 12/2002 Wahl et al. ................ 73/114.09
6,649,924 B1 * 11/2003 Philipp et al. ............... 250/554
6,882,418 B1     4/2005 Bargende

FOREIGN PATENT DOCUMENTS

JP   55-047428 A   4/1980
JP   06-167240 A   6/1994
(Continued)

OTHER PUBLICATIONS

International Search Report for PCT/JP2010/067187, dated Nov. 22, 2010.

*Primary Examiner* — Tarifur Chowdhury
*Assistant Examiner* — Jamil Ahmed
(74) *Attorney, Agent, or Firm* — Westerman, Hattori, Daniels & Adrian, LLP (57) ABSTRACT

An observation plug 102 includes a spark plug body 50, an objective optical system 10, and a set of light conduction paths 16. The spark plug body 50 ignites gas in a combustion chamber by an electric discharge in a discharge gap 60, and has an observation hole 4 penetrating in an axial direction at a location dislocated from the discharge gap 60. The objective optical system 10, which is provided in the observation hole 4 to be exposed into the combustion chamber, bends a course of light received from an incident surface 10a facing toward the discharge gap included in an observation area, and forms an image of the observation area within the observation hole 4. The set of light conduction paths 16 is provided in the observation hole 4, and divides the image of the observation area into a plurality of portions to be transmitted therethrough.

12 Claims, 5 Drawing Sheets (51) Int. Cl.
*G01J 3/02* (2006.01)
*G01J 3/36* (2006.01)
*G01J 5/00* (2006.01)
*G01N 21/67* (2006.01)
*F02P 13/00* (2006.01)
*G01J 5/60* (2006.01)
*F02P 17/00* (2006.01)

(52) U.S. Cl.
CPC ............ *G01J 5/0018* (2013.01); *G01N 21/67* (2013.01); *F02P 13/00* (2013.01); *F02P 17/00* (2013.01); *G01J 5/602* (2013.01)

(58) Field of Classification Search
USPC .................... 356/241.1; 250/554; 73/114.09
See application file for complete search history.

(56) References Cited

FOREIGN PATENT DOCUMENTS

| | | |
|---|---|---|
| JP | 10-206286 A | 8/1998 |
| JP | 2001-147157 A | 5/2001 |
| JP | 2003-515736 A | 5/2003 |
| JP | 2003-207419 A | 7/2003 |

\* cited by examiner

OBSERVATION PLUG AND SPARK OBSERVATION SYSTEM

TECHNICAL FIELD

The present invention relates to an observation plug for observing a combustion chamber, and a spark observation system that analyzes light introduced through the observation plug.

BACKGROUND ART

Conventionally, there is known an observation plug for observing a combustion chamber. For example, Patent Document 1 discloses an ignition plug having incorporated therein an image capturing device that captures an image of the inside of the combustion chamber through a visualization window. Also, Patent Document 2 discloses an in-cylinder observation device including a visualization plug provided with a lens portion exposed into a combustion chamber, and a camera provided to the lens portion via a bore scope portion. The in-cylinder observation device captures an image of the inside of the combustion chamber with the camera arranged outside the internal combustion engine.

PRIOR ART DOCUMENTS

Patent Document

Patent Document 1: Japanese Patent Application Publication No. 1998-206286
Patent Document 2: Japanese Patent Application Publication No. 2003-207419

DISCLOSURE OF THE INVENTION

Problems to be Solved by the Invention

In an internal combustion engine (for example, an automobile gasoline engine) that performs spark ignition, a flame kernel is formed and grows when spark discharge is performed, and then, the flame is propagated. The location and shape of the spark discharge influences the flame kernel. The location and shape of the flame kernel greatly influences the flame propagation. On the other hand, the locations and shapes of the spark discharge and the flame kernel change from moment to moment. Also, the locations and shapes of the spark discharge and the flame kernel change whenever the electric discharge takes place. Accordingly, it is desired to observe the locations and shapes of the spark discharge and the flame kernel.

However, in the conventional technology of observing the combustion chamber through the spark plug, since the combustion chamber is observed as a whole in order to detect the states of fuel spray and combustion, it is difficult to grasp the locations and shapes of the spark discharge and the flame kernel in the discharge gap. Also, the flame kernel, inmost cases, appears as a so-called blue flame, and provides an insufficient amount of light. With an image capturing device having a low quantum efficiency, it may be impossible to acquire a good signal-to-noise ratio, and it may be impossible to take an image of the flame kernel.

The present invention is made in view of the above-mentioned facts, and it is an object of the present invention to make it possible to successfully observe the locations and shapes of the spark discharge and the flame kernel in an observation plug for observing the combustion chamber.

Means for Solving the Problems

A first aspect of the present invention is an observation plug, comprising:
a spark plug body that ignites gas in a combustion chamber by means of an electric discharge generated in a discharge gap located in the combustion chamber, wherein the spark plug body includes an observation hole penetrating therethrough in an axial direction at a location dislocated from the discharge gap;
an objective optical system provided in the observation hole in a manner so as to be exposed into the combustion chamber, wherein the objective optical system bends a course of light received from an incident surface facing toward the discharge gap included in an observation area and forms an image of the observation area within the observation hole; and
a set of light conduction paths provided in the observation hole, wherein the set of light conduction paths causes the image of the observation area, which is to be formed by the objective optical system, to be divided into a plurality of portions and transmitted therethrough.

In accordance with a first aspect of the present invention, when an electric discharge is generated in a discharge gap of a spark plug body, a light emitted from an observation area including the discharge gap is incident upon an incident surface of an objective optical system. The objective optical system bends the course of the incident light within the inside thereof, and forms an image of the observation area inside an observation hole. A set of light conduction paths is disposed so that an incident end thereof locates at or in the vicinity of an imaging plane of the objective optical system. The set of light conduction paths divides the image of the observation area to be formed by the objective optical system into a plurality of portions and separately transmits them. According to the first aspect of the present invention, light emitted from the discharge gap is received from the incident surface facing toward the discharge gap, and the image formed from the light received through the incident surface is divided into a plurality of portions and separately transmitted.

A second aspect of the present invention is an observation plug as set forth in claim 1, wherein the spark plug body includes a central electrode and a ground electrode forming the discharge gap, in the objective optical system, the observation area is set so as to include a range from a tip of the ground electrode to a base end of the central electrode.

In accordance with a second aspect of the present invention, an observation area includes an area from a tip end of a ground electrode to a base end of a central electrode. The observation area is wider than the discharge gap by at least the width of the ground electrode and the protruded length of the central electrode.

A third aspect of the present invention is an observation plug as set forth in claim 1 or claim 2, wherein the objective optical system is constituted by an polarization prism, which firstly receives light from the observation area and bends a course of the incident light, and an imaging lens that causes outgoing light of the polarization prism to form an image.

In accordance with a third aspect of the present invention, the objective optical system is constituted by a polarization prism and an imaging lens.

A fourth aspect of the present invention is an observation plug as set forth in any one of claims 1 through 3, wherein the set of light conduction paths is configured so that optical paths from an incident surface of the objective optical system to output ends of the light conduction paths are equal to one another in length for all of the light conduction paths.

In accordance with a fourth aspect of the present invention, optical paths from an incident surface of the objective optical system to output ends of light conduction paths are equal to one another in length for all of the light conduction paths. Accordingly, light incident into the objective optical system is output from the light conduction paths in synchronization.

A fifth aspect of the present invention is an observation plug as set forth in any one of claims 1 through 4, which further comprises: an overlap prevention unit that prevents areas from which light is taken in the observation area from overlapping each other between adjacent light conduction paths in the set of light conduction paths.

In accordance with a fifth aspect of the present invention, areas from which light is taken in the observation area are prevented from overlapping each other between adjacent light conduction paths in the set of light conduction paths.

A sixth aspect of the present invention is an observation plug as set forth in anyone of claims 1 through 5, wherein a plurality of the observation holes are provided in the spark plug body at different positions around the discharge gap in a circumferential direction, and the objective optical systems and the sets of light conduction paths are respectively provided in respective observation holes.

In accordance with a sixth aspect of the present invention, the objective optical systems and the sets of light conduction paths are respectively provided in a plurality of the observation holes provided in the spark plug body at different positions around the discharge gap in a circumferential direction.

A seventh aspect of the present invention is an observation plug as set forth in claim 6, wherein from among a plurality of sets of light conduction paths provided in the respective observation holes, at least one set of light conduction paths is different from the other one or more sets of light conduction paths in the number of light conduction paths.

In accordance with a seventh aspect of the present invention, from among a plurality of sets of light conduction paths provided in the respective observation holes, at least one set of light conduction path is different from the other one or more set of light conduction path in the number of light conduction paths. The number of light conduction paths may be made variable in accordance with a direction from which the discharge gap is observed.

A eighth aspect of the present invention is a spark observation system, comprising: the observation plug as set forth in any one of claims 1 through 7; and a light analysis device that analyzes outgoing light from the set of light conduction paths and generates image information of the observation area.

In accordance with an eighth aspect of the present invention, a light analysis device is provided for the observation plug to generate image information of the observation area.

A ninth aspect of the present invention is a spark observation system as set forth in claim 8, wherein the light analysis device disperses the outgoing light from the set of light conduction paths into a plurality of wavelength components, and generates image information of the observation area for each of the wavelength components.

In accordance with a ninth aspect of the present invention, image information of the observation area is generated for each of the wavelength components dispersed from the outgoing light from the set of light conduction paths.

A tenth aspect of the present invention is a spark observation system as set forth in claim 8 or claim 9, wherein the light analysis device includes an optical sensor having a plurality of conversion elements arranged on a light receiving surface that receives the outgoing light of the set of light conduction paths, and in the optical sensor, each conversion element receives outgoing light of one single light conduction path.

In accordance with a tenth aspect of the present invention, in an optical sensor that receives an outgoing light from a set of light conduction paths, each conversion element receives outgoing light of one single light conduction path.

A eleventh aspect of the present invention is a spark observation system as set forth in claim 10, wherein optical paths from output ends of respective light conduction paths to the corresponding conversion elements are equal in length to one another for all of the conversion elements of the optical sensor.

In accordance with an eleventh aspect of the present invention, optical paths from output ends of light conduction paths to the corresponding conversion elements are equal in length to one another for all of the conversion elements.

A twelfth aspect of the present invention is a spark observation system as set forth in any one of claims 8 to 11, which further comprises a light source that radiates a reference light to the optical sensor.

In accordance with a twelfth aspect of the present invention, a light source radiates a reference light to an optical sensor.

Effects of the Invention

According to the present invention, light emitted from a discharge gap is received through an incident surface of an objective optical system facing toward the discharge gap. An image of an observation area is formed by the light received through the incident surface, divided into a plurality of portions, and transmitted by a set of light conduction paths. Using the outgoing light from the set of light conduction paths, the observation area is pixelated in a plurality of portions. Accordingly, it is possible to acquire the image of the observation area, and thus observe the locations and shapes of the spark discharge and the flame kernel. Also, since the incident surface of the objective optical system is facing toward the discharge gap, it is possible to receive a large amount of light emitted from the discharge gap. Accordingly, it is possible to successfully observe the locations and shapes of the spark discharge and the flame kernel.

In accordance with the second aspect of the present invention described above, the observation area is wider than the discharge gap by at least the width of the ground electrode and the protruded length of a central electrode. Accordingly, even if a flame kernel may stick out from the discharge gap, it is possible to observe the flame kernel.

In accordance with the fourth aspect of the present invention described above, light incident into the objective optical system is output from the set of light conduction paths in synchronization. Also, since optical path lengths are equal to one another, differences among the light conduction paths in the attenuation rate of light are small. Accordingly, it is possible to easily analyze the outgoing light from the set of light conduction paths.

In accordance with the fifth aspect of the present invention described above, in an observation area, areas from which light is received are prevented from being overlapped between light conduction paths adjacent to each other in a set of light conduction paths. As a result, light from the observation area other than a target area is prevented from entering into each light conduction path. Accordingly, it is possible to improve the observation accuracy.

In accordance with the sixth aspect of the present invention described above, light emitted from a discharge gap is received from a plurality of directions. Accordingly, it is possible to observe the discharge gap from a plurality of directions.

In accordance with the seventh aspect of the present invention described above, the number of light conduction paths included in a set of light conduction paths can be made variable in accordance with a direction from which a discharge gap is observed. The hole diameter of an observation hole may be made variable in accordance with the set of light conduction paths. Accordingly, it is possible to provide a plurality of observation holes in a relatively easy manner even though the spark plug body may be limited in space available for providing the observation holes.

In accordance with the tenth aspect of the present invention described above, in an optical sensor that receives outgoing light from a set of light conduction paths, a conversion element receives an outgoing light from one single light conduction path. The number of the conversion elements in the optical sensor can be reduced to the minimum necessary. Accordingly, it is possible to reduce the size of the optical sensor.

BEST MODE FOR CARRYING OUT THE INVENTION

In the following, a detailed description will be given of preferred embodiments of the present invention with reference to drawings. It should be noted that the following embodiments are mere examples that are essentially preferable, and are not intended to limit the scope of the present invention, applied field thereof, or application thereof.

A spark observation system 100 is used to observe a situation when a spark plug is ignited in a discharge gap. In the spark observation system 100, an area centered around the discharge gap is specified as an observation area.

<Configuration of Spark Observation System>

Figure 1:
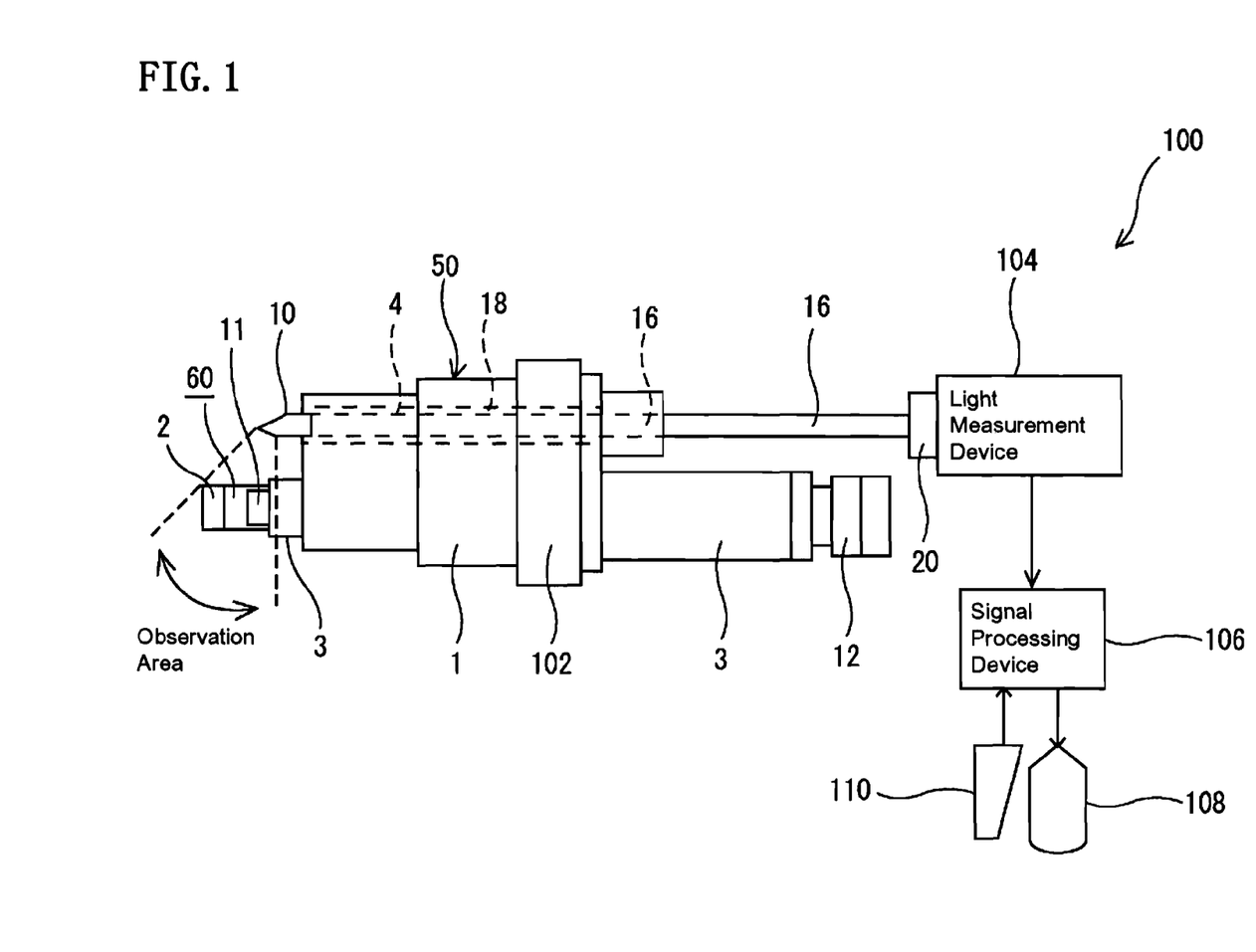
FIG. 1 is a schematic configuration diagram of a spark observation system.

The configuration of the spark observation system 100 will be described hereinafter. The spark observation system 100 is shown in FIG. 1 as including an observation plug 102, a light measurement device 104, and a signal processing device 106. The observation plug 102 is provided by retrofitting a spark plug with an objective optical system 10 and a set of light conduction paths 16. The observation plug 102 is adapted to transmit light emitted from a discharge gap 60 of a spark plug body 50 through a set of light conduction paths 16 to the outside of the combustion chamber. The light measurement device 104 is connected with a connector 20 provided at one end of the set of light conduction paths 16 and is adapted to carry out photoelectric conversion of the light transmitted through the observation plug 102 to generate a signal indicative of the intensity of the light. The signal processing device 106 is adapted to generate image information of the observation area based on the output signal from the light measurement device 104. The signal processing device 106 is connected with a monitor 108 and an operation input device 110, both of which serve as a user interface. The light measurement device 104 and the signal processing device 106 constitute a light analysis device that analyzes the outgoing light from the set of light conduction paths 16 and generates image information of the observation area. In the present embodiment, the light analysis device disperses the outgoing light from the set of light conduction paths 16 into a plurality of wavelength components, and generates image information of the observation area for each of the wavelength components.

More specifically, the observation plug 102 includes the spark plug body 50, the objective optical system 10, the set of light conduction paths 16, and the connector 20 (output terminal).

Figure 2:
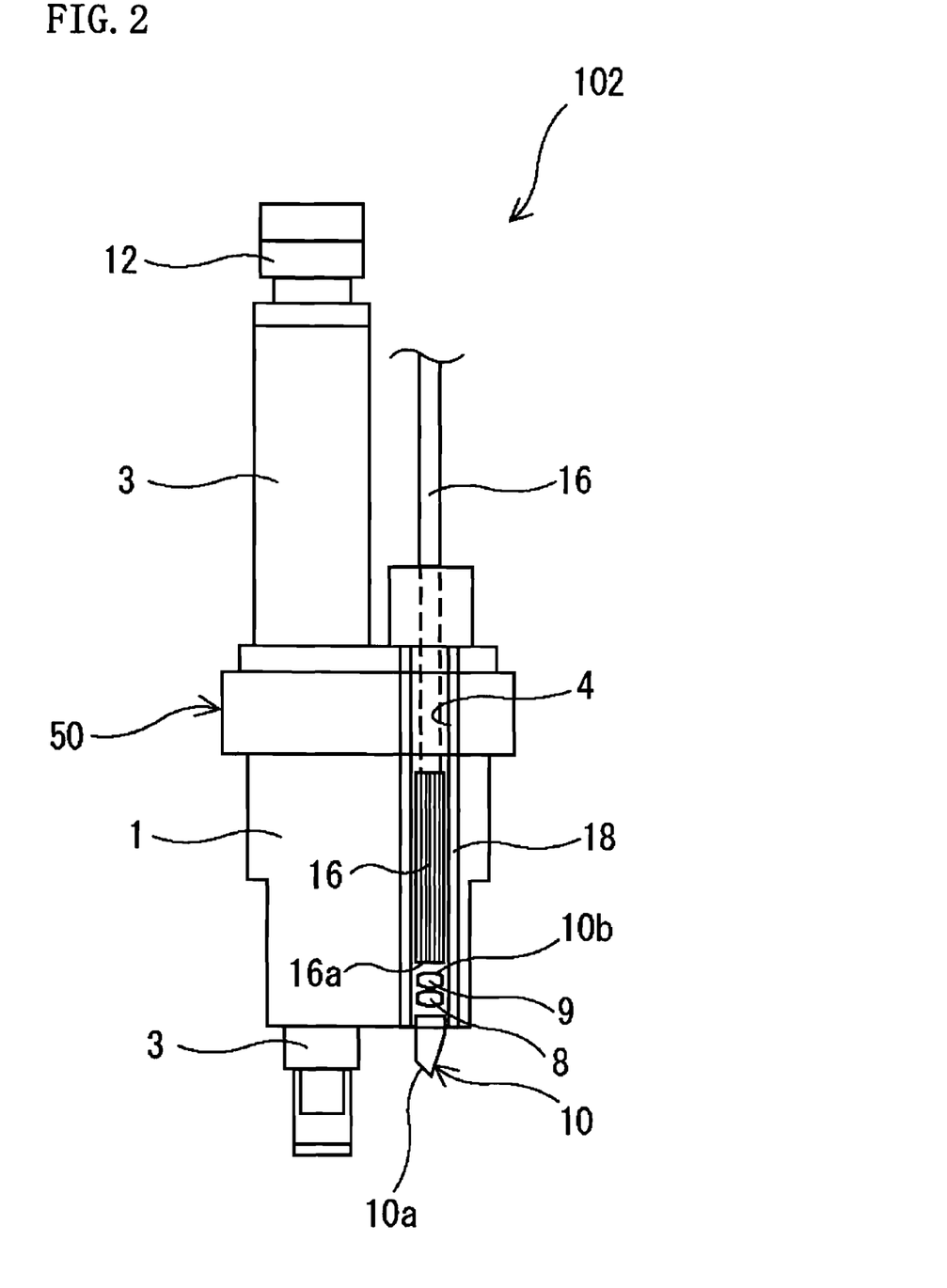
FIG. 2 is a configuration diagram of a spark observation device.

The spark plug body 50 is adapted to produce an electric discharge in a discharge gap 60 provided in a combustion chamber when a high voltage is applied between a central electrode 11 and a ground electrode 2, and thus ignite gas in the combustion chamber. As shown in FIGS. 1 and 2, the spark plug body 50 includes a central conductive body 12, a housing member 1, an insulation member 3 (insulator), and the ground electrode 2.

The central conductive body 12 is formed in a rod shape, and fitted into the inside of the insulation member 3, which is in the form of a tube shape. The both ends of the central conductive body 12 are exposed from the insulation member 3. The one end of the central conductive body 12 serves as the central electrode 11. The other end of the central conductive body 12 serves as an input terminal, to which a high voltage pulse is supplied from, for example, an ignition coil.

The housing member 1 is constituted by a conductive body in the form of a tube shape. The insulation member 3 is fitted into the inside of the housing member 1. The housing member 1 covers a portion of the side of the insulation member 3. The insulation member 3 is exposed from the both sides of the housing member 1. The insulation member 3 slightly protrudes from the discharge gap side of the housing member 1. On the other hand, almost half of the insulation member 3 protrudes from the side opposite to the discharge gap side of the housing member 1. The housing member 1 is formed with an external surface shape detachably mounted in a spark plug mounting hole of the internal combustion engine. The housing member 1 has one end connected with the ground electrode 2. The ground electrode 2 is in the form of an L shape and made of a conductive body. The ground electrode 2 forms a discharge gap 60 with the central electrode 11.

The housing member 1 is formed with an observation hole 4 (transparent hole) passing therethrough in an axial direction. The observation hole 4 is provided at a position shifted away from the discharge gap on a tip surface of the spark plug body 50. The observation hole 4 is provided on the opposite side of the discharge gap with respect to the center on the tip surface of the spark plug body 50. In the present embodiment, the observation hole 4 is constituted by an inside of a tube-shaped member 18 fitted in the through-hole of the housing member 1.

The objective optical system 10 is fixed on the side of the discharge gap 60 of the observation hole 4. Also, the set of light conduction paths 16 is inserted into the observation hole 4 from the side of the input terminal. The set of light conduction paths 16 is fixed to the housing member 1. In the observation hole 4, a light incident surface 16*a* of the set of light conduction paths 16 reaches into the vicinity of an output surface 10*b* of the objective optical system 10.

The objective optical system 10 is provided in the observation hole 4 in a manner such that the large part thereof is exposed into the combustion chamber. The objective optical system 10 is connected with the housing member 1 in a manner that closes the observation hole 4 on the side of the discharge gap 60. Accordingly, it is possible to prevent combustion gas from leaking through the observation hole 4 to the outside. The objective optical system 10 bends the course of light incident from the incident surface 10*a* facing toward the discharge gap 60 to form an image of the observation area centered on the discharge gap 60 in the observation hole 4. The objective optical system 10 is an optical system having a positive power.

The objective optical system 10 is constituted by, for example, a polarization prism 7, which light from the observation area is firstly incident upon, wherein the polarization prism 7 is adapted to bend the course of the incident light, and two imaging lenses 8, 9 that allow the outgoing light of the polarization prism 7 to form an image. In the objective optical system 10, the polarization prism 7 is exposed into the combustion chamber. The polarization prism 7 is set so that the observation area includes a range from the tip end of the ground electrode 2 to the base end of the central electrode 11.

The objective optical system 10 includes an incident surface 10*a*, which the light emitted from the discharge gap 60 is incident upon, and an output surface 10*b* directed toward the set of light conduction paths 16 in the observation hole 4. The incident surface 10*a* is provided on the polarization prism 7. The incident surface 10*a* is inclined with respect to an axis of the observation hole 4, and facing toward the discharge gap 60. The output surface 10*b* is provided on the imaging lens 9, which is the rear element of the two imaging lenses 8, 9.

Figure 3:
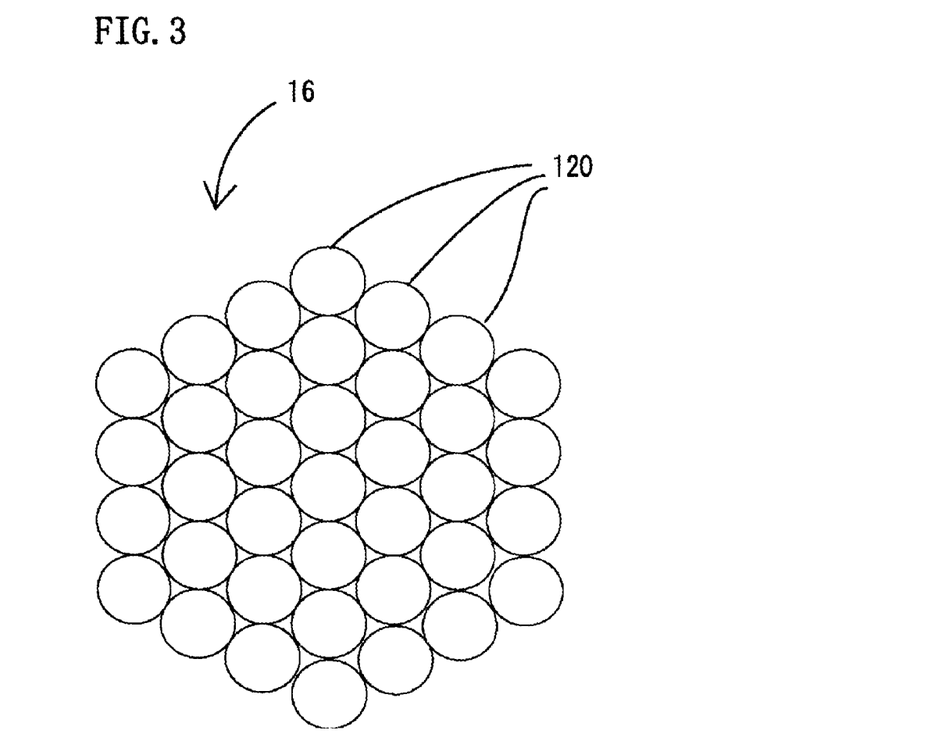
FIG. 3 is a diagram illustrating an arrangement of light conduction paths, in an incident surface of a set of light conduction paths.

The set of light conduction paths 16 is provided in the observation hole 4. The set of light conduction paths 16 is shown in FIG. 3 as including a plurality of independent light conduction paths 120. The set of light conduction paths 16 is constituted by an optical cable (for example, a bundle fiber, an image fiber, etc.) formed by bundling a plurality of optical fibers 120. In the set of light conduction paths 16, end surfaces (incident surfaces) of the respective light conduction paths 120 on the side of the objective optical system 10 are aligned on the same plane. The incident surface 16*a* of the set of light conduction paths 16 is disposed on the imaging plane of the objective optical system 10 facing toward the output surface 10*b* of the objective optical system 10. The outgoing light of the objective optical system 10 is divided into respective light conduction paths 120 of the set of light conduction paths 16. The set of light conduction paths 16 is adapted to divide the image of the observation area to be formed by the objective optical system 10 into a plurality of portions and transmit them separately.

Figure 4:
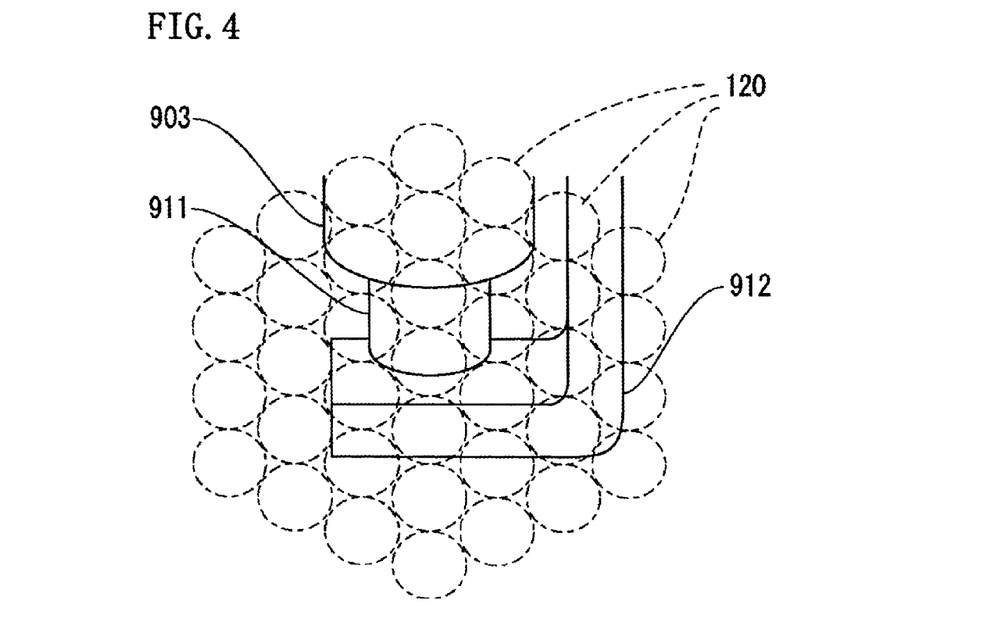
FIG. 4 is an image of an observation area formed on the incident surface of the set of light conduction paths.

FIG. 4 shows an image of the observation area, which is to be formed on the incident end surface 16*a* of the set of light conduction paths 16. The image includes an image 903 of the insulation member, an image 911 of the central electrode, and an image 912 of the ground electrode. A broken line in FIG. 4 indicates an outer circumference of the incident surface of each light conduction path 120. Each light conduction path 120 transmits light of an image formed on the incident surface thereof. The observation area in which a spark is observed is divided into a plurality of divided areas, and each light conduction path 120 transmits light taken from each of the divided areas to the outside of the combustion chamber. The light emitted from the observation area is introduced to the light conduction paths 120 for respective divided areas after being transmitted through the objective optical system 10.

Figure 5:
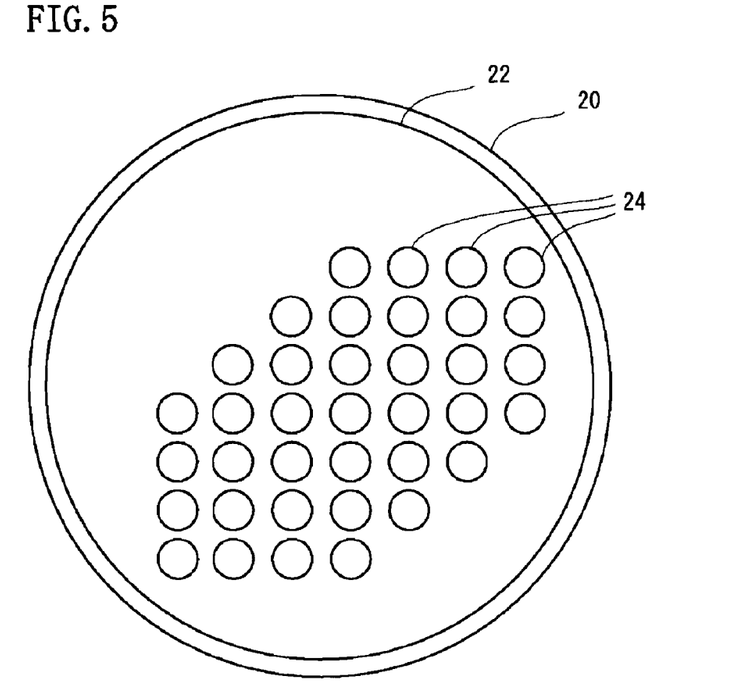
FIG. 5 is a front view of a connector.

A connector 20 is provided at an end (output end) of the set of light conduction paths 16 on the side opposite to the objective optical system 10. The connector 20 is adapted to be connected with the light measurement device 104. FIG. 5 shows the connector 20 seen from the side of the light measurement device 104. In the connector 20, the plurality of light conduction paths 120 are disposed at positions corresponding to respective grid points of square grids.

In the set of light conduction paths 16, the actual lengths of all of the light conduction paths 120 are set so that the optical path lengths from object points of the observation area (object points corresponding to light conduction paths 120) to output surfaces of the respective light conduction paths 120 are equal to one another. This ensures a synchronism among a plurality of items of optical information acquired from the observation area. Here, the object point of the observation area is intended to mean a point disposed on a plane parallel to the incident surface 10*a* of the objective optical system 10 and passing through the center of the discharge gap 60. The object point of the observation area serves as a center point of an area from which each light conduction path 120 receives light.

Figure 6:
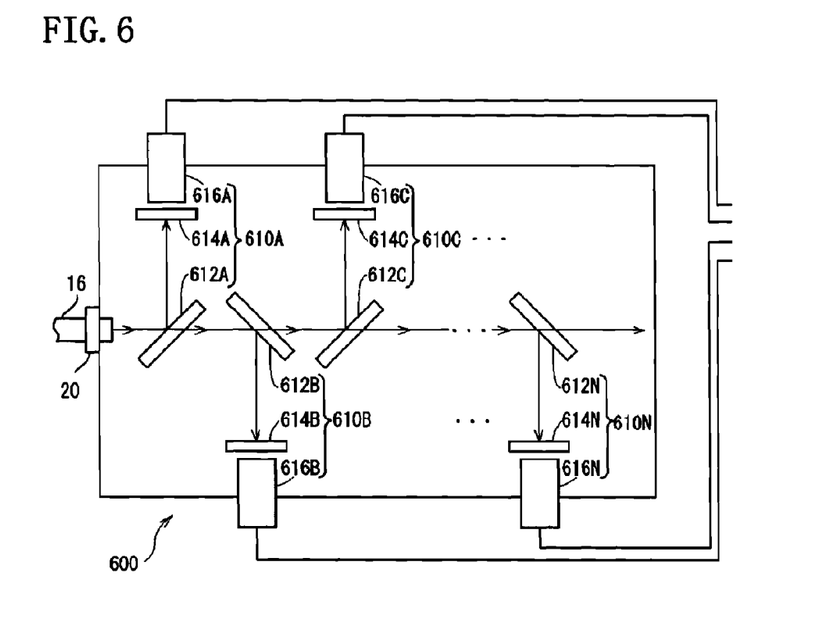
FIG. 6 is a schematic configuration diagram of a light measurement device.

FIG. 6 shows an internal configuration of the light measurement device 104. The light measurement device 104 is connected with the set of light conduction paths 16 through the connector 20. The light measurement device 104 includes a convex lens 620 (collimator) disposed on an optical axis of the outgoing light of the set of light conduction paths 16, and a plurality of spectroscopic measurement units 610A, 610B, 610C, . . . , 610N, each of which is adapted to measure the intensity of the light of a wavelength (hereinafter, referred to as a "selected wavelength") selected beforehand in accordance with a material to be measured.

The convex lens 620 has a positive power. The convex lens 620 causes the outgoing light of the set of light conduction paths 16 to form images on respective light receiving surfaces of a plurality of multianode type photomultiplier tubes 616.

Each spectroscopic measurement unit 610 is disposed on an optical axis of the outgoing light of the set of light conduction paths 16 at a predetermined angle with respect to the optical axis. Each spectroscopic measurement unit 610 includes a dichroic mirror 612A, 612B, 612C, . . . , or 612N, an interference filter 614A, 614B, 614C, . . . , or 614N, and the multianode type photomultiplier tube 616A, 616B, 616C, . . . , or 616N. In accordance with the selected wavelength, a wavelength characteristic is selected for the dichroic mirror 612 and the interference filter 614 of each spectroscopic measurement unit 610.

In the present embodiment, the selected wavelength of each spectroscopic measurement unit 610 is a wavelength corresponding to light emitted from chemical species (for example, chemical species including atoms selected from a group composed of a hydrogen atom, a carbon atom, a nitrogen atom, and an oxygen atom provided in the mixture gas) provided in the combustion chamber of the internal combustion engine. The selected wavelengths are, for example, wavelengths corresponding to light emitted from an OH radical, a CH radical, a CN radical, and a $C_2$ radical.

The selected wavelength of each spectroscopic measurement unit 610 may be a wavelength in the RGB (Red-Green-Blue) wavelength band, for example. In this case, full color information can be acquired if the outputs of all of the spectroscopic measurement units 610 are collected and examined. Also, the selected wavelength of each spectroscopic measurement unit 610 may be selected from a wavelength band corresponding to absorption lines of water, carbon dioxide, and the like. Also, the selected wavelength may be selected from a wavelength band corresponding to excitation lights of materials constituting the spark plug. Furthermore, the selected wavelength may be selected from a wavelength band corresponding to light of black-body radiation.

Each dichroic mirror 612 is adapted to exclusively reflect a light component of a predetermined band including the selected wavelength of the spectroscopic measurement unit 610. On the other hand, each dichroic mirror 612 is adapted to transmit light components outside the predetermined band to be reflected.

Each interference filter 614 is disposed on the optical axis of the light reflected from the dichroic mirror 612. Each interference filter 614 is adapted to transmit the light components of the selected wavelength of the spectroscopic measurement unit 610.

The multianode type photomultiplier tube 616 constitutes an optical sensor as having a plurality of conversion elements arranged on a light receiving surface that receives the outgoing light of the set of light conduction paths 16. The multianode type photomultiplier tube 616 is disposed on the optical axis of the light reflected from the dichroic mirror 612. The multianode type photomultiplier tube 616 is disposed on the other side of the dichroic mirror 612 with respect to the interference filter 614 intervening therebetween. In the multianode type photomultiplier tube 616 shown in FIG. 5, conversion elements that convert light into electric signals are arranged in the form of a square matrix shape. In the multianode type photomultiplier tube 616, each conversion element receives outgoing light of one single light conduction path 120. In the multianode type photomultiplier tube 616, optical paths from the output ends of the respective light conduction paths 120 to the corresponding conversion elements are made equal in length for all of the conversion elements.

As shown in FIG. 1, the signal processing device 106 is constituted by general computer hardware provided with an interface for receiving and transmitting signals with the light measurement device 104, the monitor 108, and the operation input device 110, and programs and data operating on the hardware. The operations and functions of the computer itself are publicly known and therefore, the description thereof is omitted here.

The signal processing device 106 is adapted to carry out processing and recording of the output signal from the light measurement device 104, and output the result thereof to a user. The signal processing device 106 is adapted to generate and output the image information of the observation area for the selected wavelengths using the output signals from all of the multianode type photomultiplier tubes 616.

<Operation of the Spark Observation System>

The observation operation for the spark observation system 100 that observes the observation area will be described below.

When an electric discharge takes place in the discharge gap, firstly, a flame kernel is formed. As the flame kernel grows, the combustion expands from the surrounding area toward the outside. This means that the flame propagates toward the outside. The observation operation is carried out so as to observe the locations and shapes of the spark discharge and the flame kernel.

Light emitted from the observation area is incident upon the objective optical system 10. An image of the observation area is formed on the imaging plane of the objective optical system 10, i.e., the incident surface 16*a* of the set of light conduction paths 16. The set of light conduction paths 16 divides the light received from the incident surface 16*a* into a plurality of portions and separately transmits them into the plurality of light conduction paths 120. The outgoing light of the set of the light conduction paths 16 is taken into the light measurement device 104.

In the light measurement device 104, the incident light firstly passes through the convex lens 620. Then, in each spectroscopic measurement unit 610, the dichroic mirror 612 reflects a light component having the selected wavelength. The light passing through the convex lens 620 is dispersed by the plurality of dichroic mirrors 612 for respective selected wavelengths. The light reflected from the dichroic mirror 612 passes through the interference filter 614 and reaches the multianode type photomultiplier tube 616. Upon receiving the light, the multianode type photomultiplier tube 616 sequentially converts the light components into electric signals to be outputted therefrom.

Here, the photomultiplier tube is fast in time response as a photoelectric conversion element. Therefore, it is possible to perform measurement at high time resolution. In the photomultiplier tube, photoelectric conversion is successfully performed following a short-time change of phenomena such as a spark discharge, a formation of flame kernel, and a propagation of the flame that occur in the observation area. Also, the photomultiplier tube is high in quantum efficiency. Accordingly, it is possible to perform measurement with high sensitivity. The photomultiplier tube can successfully perform photoelectric conversion of light emitting phenomena even with a small amount of light.

In the connector 20, as shown in FIG. 5, the output surfaces of the respective light conduction paths 120 are arranged on grid points of the square grids. On the other hand, in each multianode type photomultiplier tube 616, conversion elements are disposed in the form of a square matrix shape. In each multianode type photomultiplier tube 616, a distance between grid points is set so that the light conduction path 120 and the conversion element correspond to each other with one to one relationship. As a result thereof, in each multianode type photomultiplier tube 616, one conversion element receives light from one divided area (see FIG. 4) of the observation area. The output signal from each conversion element of the multianode type photomultiplier tube 616 includes information of light emitted from one single divided area, and information of the intensity of the light component of the selected wavelength of the spectroscopic measurement unit which the multianode type photomultiplier tube 616 belongs to.

Subsequently, the signal processing device 106 generates image information of the observation area for respective selected wavelengths, using the output signals of all of the multianode type photomultiplier tubes 616. The image information generated by the signal processing device 106 is displayed on the monitor 108. In the image on the monitor 108, the intensity of light in each divided area is displayed with, for example, a tone of color. Viewing this image, it is possible to recognize which kind of chemical species is dominant in the flame kernel, as well as to recognize the location and shape of the flame kernel, for example. If the selected wavelengths correspond to RGB wavelengths, a color image is output.

In a case in which the shape of arrangement of the conversion elements in the multianode type photomultiplier tube 616 is different from that of arrangement of the light conduction paths 120 in the set of light conduction paths 16, it is possible to constitute the image of the observation area by coordinate conversion or data realignment if the information of the shape of arrangement of the light conduction paths 120 of the set of light conduction paths 16 is retained in advance.

Effect of the Embodiment

In the above-described embodiment, light emitted from the discharge gap 60 is received from the incident surface 10a of the objective optical system 10 facing toward the discharge gap 60, and the light received from the incident surface 10a forms an image of the observation area. The image of the observation area is divided into a plurality of portions and transmitted through the set of light conduction paths 16. Using the outgoing light of the set of the light conduction paths 16, the observation area is pixelated in a plurality of portions, and thus, the image of the observation area can be acquired. Accordingly, it is possible to observe the locations and shapes of the spark discharge and the flame kernel. Also, since the incident surface 10a of the objective optical system 10 is disposed facing toward the discharge gap 60, it is possible to take a large amount of light emitted from the discharge gap 60. Accordingly, it is possible to successfully observe the locations and shapes of the spark discharge and the flame kernel.

Also, in the above-described embodiment, the observation area is wider than the discharge gap 60 by at least the width of the ground electrode 2 and the protruded length of the central electrode 11. Accordingly, even if the flame kernel may stick out from the discharge gap 60, it is possible to observe the flame kernel.

Furthermore, in the above-described embodiment, in the multianode type photomultiplier tube 616 that receives the outgoing light of the set of light conduction paths 16, each conversion element receives an outgoing light from one light conduction path 120. The number of the conversion elements in the multianode type photomultiplier tube 616 can be reduced to the minimum necessary. Accordingly, it is possible to reduce the size of the photomultiplier tubes 616.

Also, in the above-described embodiment, flexible optical fibers are used as the light conduction paths 120 from the observation area to the light measurement device 104. As a result, the light conduction paths 120 are resistant to damage caused by vibration of the internal combustion engine.

Furthermore, in the above-described embodiment, on the output surface of the set of light conduction paths 16, the light conduction paths 120 are arranged in conformity with the arrangement of the conversion elements of the multianode type photomultiplier tube 616. Accordingly, since the conversion elements are located at positions corresponding to the positions where the respective light conduction paths 120 receive light from the observation area, it is possible to easily generate image information of the observation area.

Other Embodiments

The above-described embodiment can also be configured as follows.

In the above-described embodiment, the set of light conduction paths 16 may be configured so that the optical paths from the incident surface 10a of the objective optical system 10 to the output ends of the light conduction paths 120 are equal in length for all of the light conduction paths 120. In this case, light incident into the objective optical system 10 is output from the set of light conduction paths 16 in synchronization. Since the optical paths are equal in length to one another, differences in the attenuation rate of light among the light conduction paths 120 are small. Accordingly, it is possible to easily analyze the outgoing light of the set of light conduction paths 16.

Figure 7:
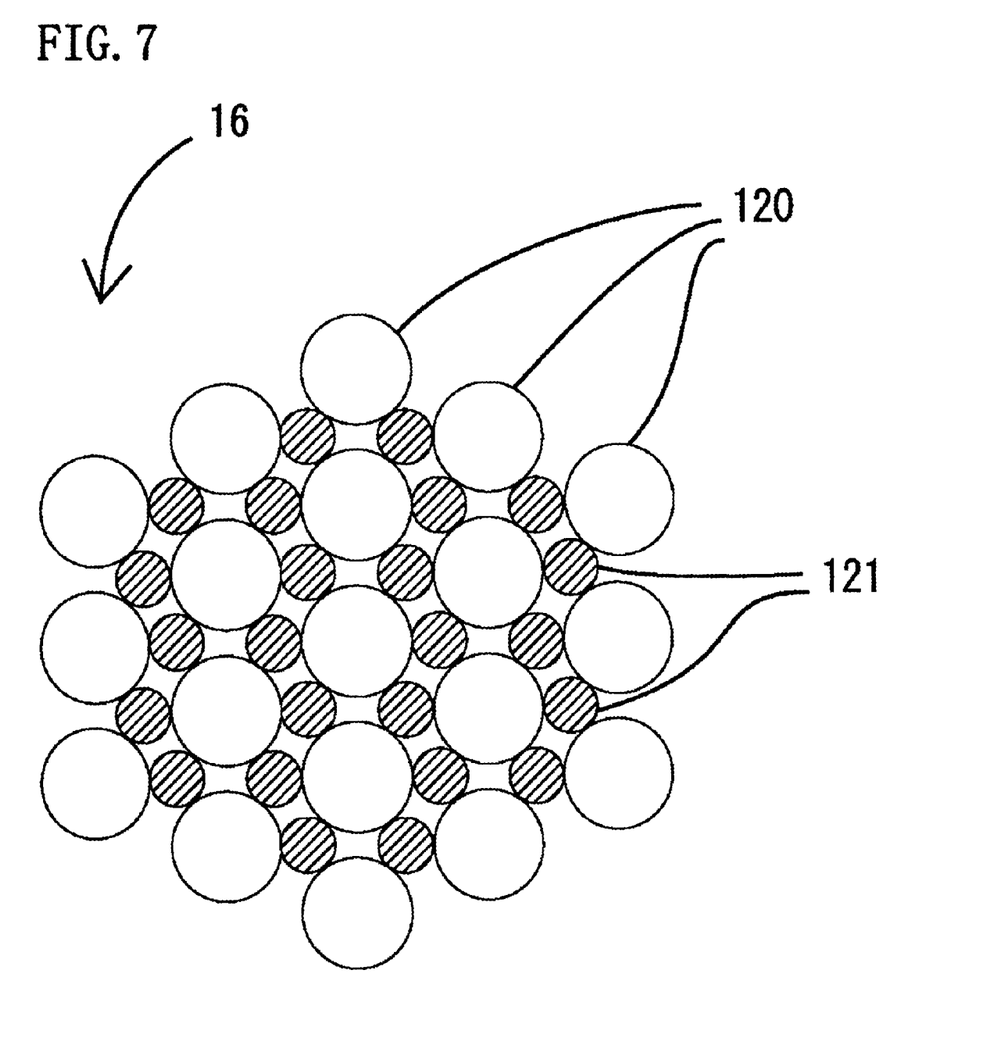
FIG. 7 is a front view of the incident surface of the set of light conduction path in other embodiments.

Also, in the above-described embodiment, it is possible to provide an overlap prevention unit that prevents areas from which light is taken in the observation area from overlapping each other between adjacent light conduction paths 120 in the set of light conduction paths 16. As shown in FIG. 7, the overlap prevention unit is constituted by a plurality of linear members 121 provided among the light conduction paths 120. The overlap prevention unit serves to have adjacent light conduction paths 120 spaced apart from one another in the set of light conduction paths 16 so as to keep the adjacent light conduction paths 120 spaced apart from each other at a constant distance. In this manner, it is possible to prevent light from the observation area other than the corresponding target area from entering into each light conduction path 120. Accordingly, it is possible to improve the observation accuracy.

Also, in the spark plug body 50 of the above-mentioned embodiment, a plurality of observation holes 4 may be provided around the discharge gap 60 at positions different from one another in the circumferential direction, and objective optical systems 10 and sets of light conduction paths 16 may be provided in the respective observation holes 4. In this case, light measurement devices 104 are connected with respective sets of light conduction paths 16, and the output signals of all of the light measurement devices 104 are processed by the signal processing device 106. In this manner, light emitted from the discharge gap 60 is received from a plurality of directions, thereby making it possible to observe the discharge gap 60 from the plurality of directions. In this configuration, from among a plurality of sets of light conduction paths 16 provided in the respective observation holes 4, the number of light conduction paths 120 may vary from one set of light conduction paths 16 to another. In this manner, the number of light conduction paths 120 included in the set of light conduction paths 16 may be made variable in accordance with a direction from which the discharge gap 60 is observed. The hole diameter of the observation hole 4 may be made variable in accordance with the set of light conduction paths 16. Accordingly, it is possible to provide a plurality of observation holes 4 in a relatively easy manner even though the spark plug body 50 may be limited in space available for providing the observation holes 4.

Also, in the above-mentioned embodiment, a light source that radiates a reference light to the multianode type photomultiplier tube 616 serving as the optical sensor may be provided.

Also, in the above-mentioned embodiment, the light measurement device 104 separates wavelengths by a filter bank method. The wavelengths may be separated using an optical device such as, a diffraction grating, a prism, or the like, that polarizes light in accordance with a wavelength. In this case, in the connector 20, output end surfaces of respective light conduction paths 120 are aligned on a line perpendicular to a polarization plane of the optical device for polarization. Also, as the multianode type photomultiplier tube, an array type is selected, and elements thereof are aligned on a line perpendicular to a polarization plane of the optical device for polarization. In addition, there are various methods of wavelength separation, any one of which may be selected as appropriate.

Also, in the above-mentioned embodiment, each light conduction path 120 has a portion inserted into the observation hole 4. The inserted portion may be formed by a hollow tube. In this case, a rod lens or a refractive index distribution lens may be inserted into the hollow tube.

Also, in the above-described embodiment, the light analysis device constituted by the light measurement device 104 and the signal processing device 106 may generate image information of the observation area from the outgoing light of the set of light conduction paths 16 as is without separating it for respective wavelengths thereof.

Also, in the above-described embodiment, the light measurement device 104 may separately amplify and output the output signals of the multianode type photomultiplier tubes 616.

Furthermore, in the above-described embodiment, light conduction paths 120 may be respectively constituted by a plurality of optical fibers (for example, a bundle fiber, an imaging fiber, etc.).

INDUSTRIAL APPLICABILITY

As described in the above, the present invention is useful for an observation plug that allows observation of a combustion chamber, and a spark observation system that analyzes light taken from the observation plug.

EXPLANATION OF REFERENCE NUMERALS 1 housing member
2 ground electrode
3 insulation member
4 observation hole
11 central electrode
12 central conductive body
16 set of light conduction paths
100 spark observation system
102 observation plug
104 light measurement device
106 signal processing device
120 light conduction path

The invention claimed is:
1. An observation plug, comprising:
a spark plug body that ignites gas in a combustion chamber by means of an electric discharge generated in a discharge gap located in the combustion chamber, wherein the spark plug body includes an observation hole penetrating therethrough in an axial direction at a location dislocated from the discharge gap;
an objective optical system which is provided in the observation hole and which has an incident surface which faces toward the discharge gap, thereby including the discharge gap in an observation area of the objective optical system, wherein the objective optical system bends a course of light received from the incident surface and forms an image of the observation area within the observation hole; and
a set of light conduction paths provided in the observation hole, wherein the set of light conduction paths causes the image of the observation area, which is to be formed by the objective optical system, to be divided into a plurality of portions and transmitted therethrough.

2. An observation plug as set forth in claim 1, wherein
the spark plug body includes a central electrode and a ground electrode forming the discharge gap,
in the objective optical system, the observation area is set so as to include a range from a tip of the ground electrode to a base end of the central electrode, and
at least a portion of the objective optical system is exposed from the spark plug body into the combustion chamber.

3. An observation plug as set forth in claim 1 or claim 2, wherein
the objective optical system is constituted by an polarization prism, which firstly receives light from the observation area and bends a course of the incident light, and an imaging lens that causes outgoing light of the polarization prism to form an image.

4. An observation plug as set forth in claim 3, wherein
the set of light conduction paths is configured so that optical paths from an incident surface of the objective optical system to output ends of the light conduction paths are equal to one another in length for all of the light conduction paths.

5. An observation plug as set forth in claim 4, which further comprises:
an overlap prevention unit that prevents areas from which light is taken in the observation area from overlapping each other between adjacent light conduction paths in the set of light conduction paths.

6. An observation plug as set forth in claim 5, wherein
a plurality of the observation holes are provided in the spark plug body at different positions around the discharge gap in a circumferential direction, and
the objective optical systems and the sets of light conduction paths are respectively provided in respective observation holes.

7. An observation plug as set forth in claim 6, wherein
from among a plurality of sets of light conduction paths provided in the respective observation holes, at least one set of light conduction paths is different from the other one or more sets of light conduction paths in the number of light conduction paths.

8. A spark observation system, comprising:
the observation plug as set forth in claim 7; and
a light analysis device that analyzes outgoing light from the set of light conduction paths and generates image information of the observation area.

9. A spark observation system as set forth in claim 8, wherein
the light analysis device disperses the outgoing light from the set of light conduction paths into a plurality of wavelength components, and generates image information of the observation area for each of the wavelength components.

10. A spark observation system as set forth in claim 9, wherein
the light analysis device includes an optical sensor having a plurality of conversion elements arranged on a light receiving surface that receives the outgoing light of the set of light conduction paths, and in the optical sensor, each conversion element receives outgoing light of one single light conduction path.

11. A spark observation system as set forth in claim 10, wherein optical paths from output ends of respective light conduction paths to the corresponding conversion elements are equal in length to one another for all of the conversion elements of the optical sensor.

12. A spark observation system as set forth in claim 11, which further comprises a light source that radiates a reference light to the optical sensor.

* * * * *